United States Patent [19]

Atkinson et al.

[11] Patent Number: 4,634,766
[45] Date of Patent: Jan. 6, 1987

[54] 1,4-DIAZA-PHENOTHIAZINES

[75] Inventors: Joseph G. Atkinson, Montreal; Yvan Guindon, Closse Ile Bizard; Patrice C. Bélanger, Dollard des Ormeaux; Joshua Rokach, Laval, all of Canada

[73] Assignee: Merck Frosst Canada, Inc., Kirkland, Canada

[21] Appl. No.: 660,595

[22] Filed: Oct. 15, 1984

Related U.S. Application Data

[63] Continuation-in-part of Ser. No. 547,161, Oct. 31, 1983, abandoned.

[51] Int. Cl.⁴ .................. C07D 498/04; C07D 513/04
[52] U.S. Cl. ........................................ 544/34; 544/101
[58] Field of Search ........................................... 544/34

[56]  References Cited

U.S. PATENT DOCUMENTS 3,746,707  7/1973  Gulbenk et al. ...................... 544/34
3,845,044  10/1974  Tong ..................................... 544/34
4,552,874  11/1985  Mardin et al. ...................... 514/222

FOREIGN PATENT DOCUMENTS 0085881  1/1983  European Pat. Off. .
430462  4/1976  U.S.S.R. .

OTHER PUBLICATIONS

Carter, Chemical Abstracts, vol. 87, (1977), 152146m.
Cheeseman et al, Tetrahedron, vol. 36, (1980), pp. 2681-2683.
Okafor, J. Het. Chem., vol. 18, (1981), pp. 405-407.
Journal of Medicinal Chemistry, 1983, pp. 564-569; W. S. Saari et al.
Carter et al., Tetrahedron, vol. 33(8), (1977), pp. 827-832.

Primary Examiner—Richard L. Raymond
Attorney, Agent, or Firm—Gabriel Lopez; Hesna J. Pfeiffer; Paul H. Ginsburg

[57]  ABSTRACT

Compounds of the Formula I:

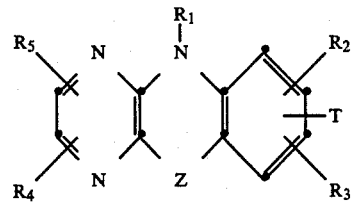

are inhibitors of the mammalian 5-lipoxygenase enzyme system of the arachidonic acid cascade. As such, these compounds are useful therapeutic agents for treating allergic conditions, asthma, cardiovascular disorders and inflammation.

8 Claims, No Drawings

1,4-DIAZA-PHENOTHIAZINES

This application is a continuation-in-part of U.S. Ser. No. 547,161, filed Oct. 31, 1983, now abandoned.

This invention is directed to inhibitors of the 5-lipoxygenase enzyme system of the arachidonic acid cascade. Inhibition of 5-lipoxygenase prevents the biosynthesis of the leukotrienes.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthamatic lungs. 5-Lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. 5-Lipoxygenase inhibitors would therefore be a new class of drugs for the treatment of asthma.

Psoriasis is a human skin disease which effects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amount of lipoxygenase products. Leukotriene $B_4$ has been deteected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function. See, for example, B. Samuelson, *Science*, 220, 568 (1983).

Several compounds having the Formula A (especially wherein $Z=S$) are taught in the literature as pesticides and herbicides:

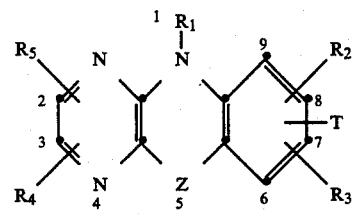

see for example: S. D. Carter et al., *Tetrahedron* 33 827 (1977); G. W. H. Cheeseman et al., *Tetrahedron* 36 2681 (1980); C. O. Okafor, *Het. Chem.* 18 405–407 and 1445–1449 (1981); and U.S. Pat. Nos. 3,663,543; 3,746,707; 3,808,208; 3,821,213 and 3,845,044. None of the compounds of Formula A are taught to have 5-lipoxygenase inhibiting properties.

It has been discovered that compounds of the Formula A are effective inhibitors of leukotriene biosynthesis via inhibition of the mammalian 5-lipoxygenase enzyme system. Thus, these compounds are useful therapeutic agents for treating conditions such as asthma, allergies, cardiovascular disorders such as angina and inflammation, and skin diseases such as psoriasis.

The compounds of the present invention may also be used to treat or prevent mammalian (especially human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt incuded pancreatic or gastric damage; trauma- or stress-induced cell damage; and glycerol-induced renal failure.

The present invention relates to pharmaceutical compositions containing a compound of the Formula I:

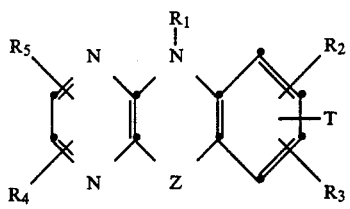

or a pharmaceutically acceptable salt thereof, a method of treatment using said composition and novel compounds encompassed by Formula I.

One embodiment of the present invention is a pharmaceutical composition useful for inhibiting leukotriene biosynthesis or action containing a compound of the Formula I:

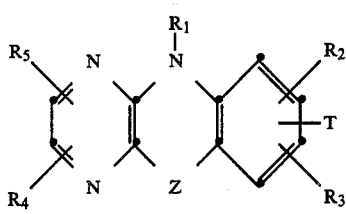

or a pharmaceutically acceptable salt thereof and a pharmaceutically acceptable carrier, wherein:

Z is O, NCN, S, SO or $SO_2$;

$R_1$ is H, $C_1$ to $C_6$ alkyl, benzyl, $C_1$ to $C_6$ acyl, $C_1$ to $C_6$ lower aminoacyl, $C_1$ to $C_6$ alkylacyloxy-$C_1$ to $C_6$ alkyl (for example, —$CH(CH_3)OCOC(CH_3)_3$), $C_1$ to $C_6$ alkoxy-$C_1$ to $C_6$ alkyl (for example, —$CH(CH_3)OC_2H_5$), —$(CH_2)_n COOR_6$(wherein n is)0 to 4, CN, $C_1$ to $C_6$(alkylacyloxy-$C_1$) to $C_6$ alkoxycarbonyl (e.g. —$COOCH(O_2CCH_3)CH_3$), —$C(R_7)=C(R_7)COOR_6$ or $SO_2R_{10}$; $R_2$, $R_3$, $R_4$ and $R_5$ are each independently selected from:

(1) hydrogen;
(2) $C_1$ to $C_6$ alkyl;
(3) $C_2$ to $C_6$ alkenyl;
(4) —$(CH_2)_nM$ wherein:
  n is 0 to 6 and
  M is
   (a) $OR_{16}$;
   (b) halogen;
   (c) $CF_3$;
   (d) $SR_{16}$;
   (e) phenyl;
   (f) substituted phenyl wherein substituted phenyl is as defined in the definition of $R_{16}$;
   (g) $COOR_6$;
   (h)

(i) tetrazole;
   (j)

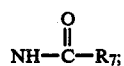

(k) $NR_8R_9$;
   (l) $NHSO_2R_{10}$;

(m)

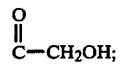

(n) $SOR_{11}$ wherein $R_{11}$ is $C_1$ to $C_6$ alkyl, phenyl, substituted phenyl wherein substituted phenyl is as defined in the definition of $R_{16}$, $(CH_2)_mCOOR_6$ wherein m is 1 to 6, or $CF_3$;
   (o) $CONR_8R_9$;
   (p) $SO_2NR_8R_9$;
   (q) $SO_2R_{13}$ wherein $R_{13}$ is OH, $C_1$ to $C_6$ alkyl, H, phenyl, substituted phenyl wherein substituted phenyl is as defined in the definition of $R_{16}$, $(CH_2)_mCOOR_6$ wherein m is 1 to 6, or $CF_3$;
   (r) $NO_2$;
   (s)

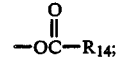

(t)

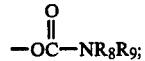

(u)

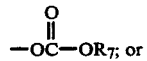

(v) —CN:

each $R_{16}$ is independently H; $C_1$ to $C_6$-alkoxy-$C_1$ to $C_6$ alkyl; $C_1$ to $C_6$ alkylacyloxy-$C_1$ to $C_6$ alkyl; $C_1$ to $C_6$ alkyl; substituted phenyl wherein the substituents are $C_1$ to $C_3$ alkyl, halogen, CN, $C_1$ to $C_3$ alkoxy, OH, $(CH_2)_nNR_8R_9$ wherein n is 0 to 2, $CF_3$, $COOR_6$, $CH_2COOR_6$; —$(CH_2)_mCOOR_6$ wherein m is 0 to 6; CN; $C_1$ to $C_5$ alkylacyl; $C_1$ to $C_4$ perfluoroalkyl; phenyl; benzyl; or $CH_2$—$R_{12}$ wherein $R_{12}$ is $C_1$ to $C_5$ alkyldimethylamino;

each $R_6$ is independently H, $C_1$ to $C_6$ alkyl, benzyl or phenyl;

each $R_{14}$ is independently H, $C_1$ to $C_6$ alkyl, $C_1$ to $C_6$ alkoxy, $C_1$ to $C_6$ alkylacyloxy-$C_1$ to $C_6$ alkoxy, $(CH_2)_nCOOR_6$ wherein n is 0 to 4, phenyl, substituted phenyl wherein substituted phenyl is as defined in the definition of $R_{16}$, or is such that $R_{14}COOH$ is an essential amino acid;

each $R_8$ and $R_9$ is independently H, phenyl, substituted phenyl wherein substituted phenyl is as defined in the definition of $R_{16}$, or $C_1$ to $C_4$ alkyl, or $R_8$ and $R_9$ may be joined through the N to form a heterocycloalkyl of 5 to 8 ring atoms (for example, pyrrolidino, piperidino); and each $R_7$ is independently H, $C_1$ to $C_6$ alkyl, benzyl, phenyl or $C_1$ to $C_6$(alkylacyloxy-$C_1$) to $C_6$ alkoxy;

each $R_{10}$ is indpendently OH, $C_1$ to $C_6$ alkyl, $C_1$ to $C_6$ alkoxy, phenyl or p-tolyl;

or any two of $R_1$, $R_2$, $R_3$, $R_4$ or $R_5$ may be joined to form an additional ring of 5 to 7 members, said ring optionally containing a carbonyl group as a substituent, optionally containing a hydroxyl group as a substituent, and optionally having 1 or 2 double bonds, wherein if $R_1$ is a constituent of the ring, one member is nitrogen and the others are carbon and if $R_1$ is not a constituent of the ring, all the members are carbon; and T is hydrogen or $OR_{15}$ wherein $R_{15}$ is hydrogen, $C_1$ to $C_6$ alkyl, $C_1$ to $C_6$ alkylacyl, phenyl-$C_1$ to $C_8$-alkylacyl, $SO_2R_{10}$, arylsulfonyl, —CO-phenyl or substituted phenyl wherein substituted phenyl is as defined in the definition of $R_{16}$.

A preferred embodiment of the Formula I compounds is one wherein Z is O, S, SO or $SO_2$ and wherein n is 0 or 1 in the unit —$(CH_2)_nM$. A more preferred embodiment is wherein Z is O, S, SO or $SO_2$ and wherein n is 0 (zero) in the unit —$(CH_2)_nM$. In both of these embodiments, the remaining substituents are as defined for Formula I.

Another preferred embodiment of the Formula I compounds is one wherein:

Z is O or S;

$R_1$ is H, $C_1$ to $C_6$ alkyl, $C_1$ $C_6$ acyl, —$(CH_2)_nCOOR_6$ wherein n is 0 to 4, $C_1$ to $C_6$ alkylacyloxy-$C_1$ to $C_6$ alkoxycarbonyl (e.g. —$COOCH(O_2CCH_3)CH_3$), —$C(H)=C(H)COOR_6$, or $SO_2R_{10}$;

$R_2$, $R_3$, $R_4$ and $R_5$ are each independently selected from:
(1) hydrogen;
(2) $C_1$ to $C_6$ alkyl;
(3) —$(CH_2)_nM$ wherein:
n is 0 and
M is
(a) $OR_{16}$;
(b) halogen
(c) $CF_3$;
(d) $NO_2$;
(e)

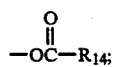

(f)

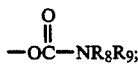

(g)

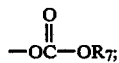

each $R_{16}$ is independently H; $C_1$ to $C_6$-alkoxy-$C_1$ to $C_6$ alkyl; $C_1$ to $C_6$alkylacyloxy-$C_1$ to $C_6$ alkyl;

Cl to $C_6$ alkyl; benzyl; phenyl; substituted phenyl wherein the substituents are $C_1$ to $C_3$ alkyl, halogen, CN, $C_1$ to $C_3$ alkoxy, OH, $(CH_2)_nNR_8R_9$ wherein n is 0 to 2, $CF_3$, $COOR_6$, $CH_2COOR_6$; —$(CH_2)_mCOOR_6$ wherein m is 0 to 6; CN; $C_1$ to $C_5$ alkylacyl; $C_1$ to $C_4$ perfluoroalkyl; or $CH_2$—$R_{12}$ (wherein $R_{12}$ is $C_1$ to $C_5$ alkyldimethylamino;)

each $R_6$ is independently H, $C_1$ to $C_6$ alkyl, benzyl or phenyl;

each $R_{14}$ is independently H, $C_1$ to $C_6$ alkyl, $C_1$ to $C_6$ alkoxy, $C_1$ to $C_6$ alkylacyloxy-$C_1$ to $C_6$ alkoxy, $(CH_2)_nCOOR_6$ wherein n is 0 to 4, phenyl, substituted phenyl wherein substituted phenyl is as defined in the definition of $R_{16}$, or is such that $R_{14}COOH$ is an essential amino acid;

each $R_8$ and $R_9$ is independently H, phenyl, substituted phenyl wherein substituted phenyl is as defined in the definition of $R_{16}$ or $C_1$ to $C_4$ alkyl, or $R_8$ and $R_9$ may be joined through the N to form a heterocycloalkyl of 5 to 8 ring atoms (for example, pyrrolidino, piperidino); and each $R_7$ is independently H, $C_1$ to $C_6$ *alkyl, benzyl, phenyl* or $C_1$ to $C_6$ alkylacyloxy-$C_1$ to $C_6$ alkoxy; and each $R_{10}$ is independently OH, $C_1$ to $C_6$ alkyl, $C_1$ to $C_6$ alkoxy, phenyl or p-tolyl;

T is hydrogen or $OR_{15}$ wherein $R_{15}$ is hydrogen, $C_1$ to $C_6$ alkyl, $C_1$ to $C_6$ alkylacyl, phenyl-$C_1$ to $C_8$-alkylacyl, $SO_2$ $R_{10}$, arylsulfonyl, —CO-phenyl or substituted phenyl wherein substituted phenyl is as defined in the definition of $R_{16}$;

with the proviso that there is a group $OR_{16}$ located at one of the 6, 7, 8 or 9-positions.

The term alkyl, as used herein, includes straight chain, branched chain and cyclic groups.

The term aryl, as used herein, includes phenyl, naphthyl, anthracenyl, and the like.

The term heteroaryl includes 5- and 6-membered rings containing at least one heteroatom selected from N, O, S, for example, furyl, thienyl, pyrrolyl, pyridyl.

The term essential amino acid is employed to include the following amino acids; lysine, tryptophan, histidine, phenylalanine, leucine, isoleucine, threonine, methionine, valine, arginine, alanine, proline, glycine, serine, cysteine, tyrosine, asparagine, glutamine, aspartic acid and glutamic acid.

Whenever possible, appropriate pharmaceutically acceptable salts of Formula I are included within the definitions given above. These include carboxylic or mineral acid addition salts where Formula I is basic and salts of pharmaceutically acceptable bases when Formula I is acidic. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, trimethamine, choline and caffeine.

When the compound is basic, salts may be prepared from pharmaceutically acceptable non-toxic acids, including inorganic and organic acids. Such acids include hydrochloric, hydrobromic, sulfuric, nitric, isethionic, methanesulfonic, ethanesulfonic, benzenesulfonic, p-tolueuesulfonic, acetic, benzoic, comphorsulfonic, citric, fumaric, gluconic, glutamic, lactic, malic, maleic, mandelic, mucic, pamoic, pantothenic, phosphoric, succinic; tartaric acid and the like. Particularly preferred are hydrochloric, hydrobromic, citric, maleic, phosphoric, sulfuric and tartaric acids.

For a helpful discussion of pharmaceutical salts see S. M. Berge et al., Journal of Pharmaceutical Sciences, 66, 1-19 (1977), the disclosure of which is hereby incorporated herein by reference.

The compounds of the present invention are prepared by a series of reactions as illustrated in Scheme I. An initial condensation reaction between a vicinal dihalopyrazine (III) with an appropriately substituted aminobenzenethiol (IV) affords the compound (V).

Compound (V) is cyclized in the presence of a base, such as triethylamine and an inert solvent such as dimethylformamide (DMF) to afford the compound of Formula I wherein Z=S.

Compounds of Formula I wherein Z=S may be oxidized by contacting the Formula I compounds with 30-35% hydrogen peroxide in an acidic solvent for several hours at a temperature of from about 75° to 80° C. In some cases, higher peroxide concentrations, higher temperatures and/or more prolonged contact times may be required, especially when the sulfone is the desired product. Acetic acid is generally a useful solvent, but other acids, such as trifluoroacetic acid, can also be employed.

Similarly, the compounds of Formula I wherein Z=O or NCN may be produced by following Scheme I, but substituting the appropriate compound corresponding to Formula (IV) for the aminobenzenethiol shown.

It will be obvious to the skilled artisan that the substituents present in the compounds of formulae III, IV and V must be such that they are compatible with the reaction conditions used in the preparation of Formula I.

SCHEME I

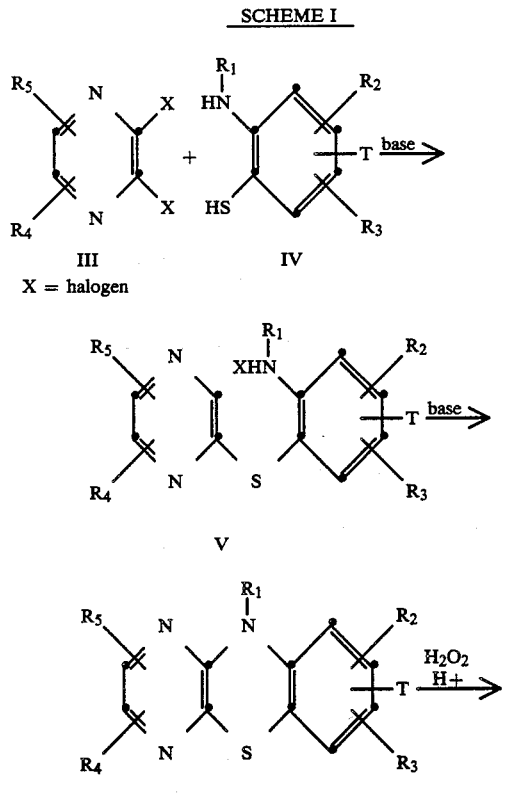

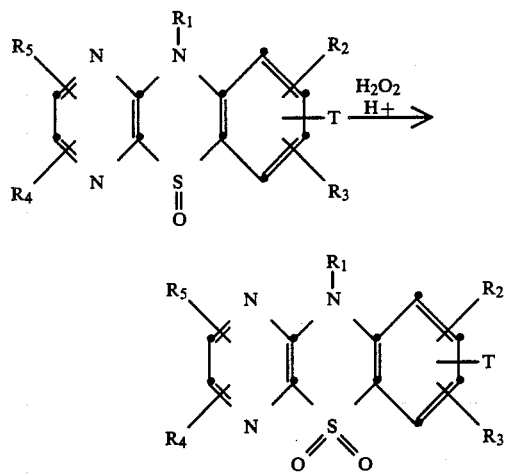

An alternative procedure for preparing compounds of Formula I substituted at position 10 is illustrated in Scheme II. Thus, an alkylating agent is reacted with a compound of Formula VI in the presence of a base in an inert solvent to yield compounds of Formula I. A side product of Formula VII, resulting from alkylation at position I is sometimes obtained in this reaction.

SCHEME II

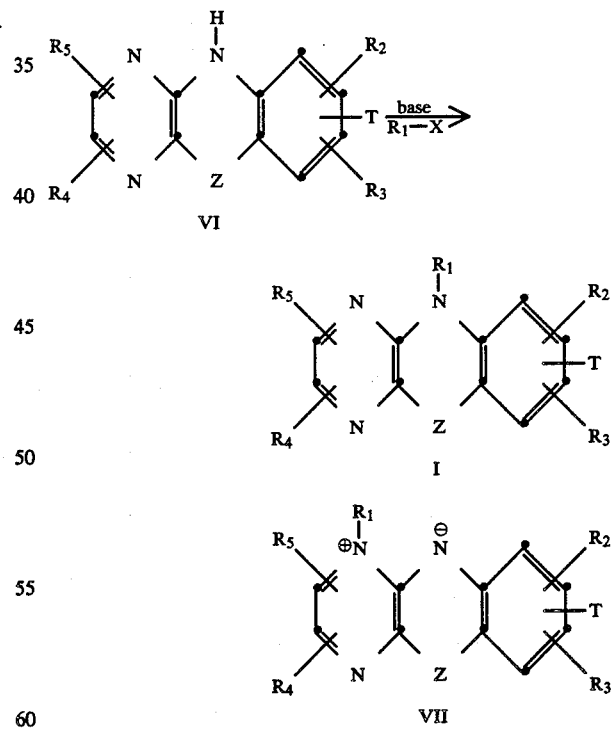

The compounds of the Formula I have unexpected activity as inhibitors of the mammalian biosynthesis of leukotriene $B_4$, as well as leukotrienes $C_4$, $D_4$, $E_4$ and $F_4$, the active elements of the slow reacting substance of anaphylaxis (SRS-A). The compounds of Formula I act as inhibitors of the mammalian 5-lipoxygenase enzyme system of the arachidonic acid cascade. This inhibition of the mammalian biosynthesis of leukotrienes indicates that the compositions are useful to treat, prevent or ameliorate, in mammals and especially in humans (1) pulmonary conditions including diseases such as asthma, (2) allergies and allergic reactions such as allergic rhinitis, contact dermatitis, allergic conjunctivitis and the like, (3) inflammation such as arthritis, (4) pain, (5) skin conditions such as psoriasis and the like and (6) cardiovascular conditions such as angina and the like.

Examples of the Formula I compounds useful in the present compositions are tabulated in Table I. The number preceding the $R_2$–$R_5$ and T definitions signifies that group's position on the ring system.

inhibiting activity and other relevant biological activities.

Rat Polymorphonuclear Leukocyte (P.M.N.) Assay

Rats under ether anesthesia were injected (i.p.) with 8 ml of a suspension of sodium caseinate (6 grams in ca. 50 ml water). After 15–24 hours the rats were sacrificed ($CO_2$) and the cells from the peritoneal cavity were recovered by lavage with 20 ml of buffer (Eagles MEM containing 30 mM HEPES adjusted to pH 7.4 with NaOH). The cells were pelleted (350×g, 5 min.), resuspended in buffer with vigorous shaking, filtered through lens paper, recentrifuged and finally suspended

TABLE I

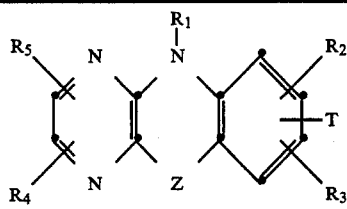

| Compound | Z | $R_1$ | $R_2$ | $R_3$ | $R_4$ | $R_5$ | T |
|---|---|---|---|---|---|---|---|
| 1 | S | H | H | H | H | H | H |
| 2 | S | $CH_3$ | H | H | H | H | H |
| 3 | S | $CH_2Ph$ | H | H | H | H | H |
| 4 | S | H | 3-$NO_2$ | H | H | H | H |
| 5 | S | H | 2-Cl | 3-Cl | H | H | H |
| 6 | S | H | 3-$NO_2$ | 7-$NO_2$ | H | H | H |
| 7 | S | $CH_3$ | 2-$NO_2$ | H | H | H | H |
| 8 | S | $CH_3$ | 3-$NO_2$ | H | H | H | H |
| 9 | S | n-$C_3H_7$ | 2-Cl | 3-Cl | H | H | H |
| 10 | S | n-$C_6H_{13}$ | 2-Cl | 3-Cl | H | H | H |
| 11 | S | $CH_2Ph$ | 2-Cl | 3-Cl | H | H | H |
| 12 | SO | H | H | H | H | H | H |
| 13 | SO | $CH_3$ | H | H | H | H | H |
| 14 | SO | H | 2-Cl | 3-Cl | H | H | H |
| 15 | SO | H | 3-$NO_2$ | 7-$NO_2$ | H | H | H |
| 16 | $SO_2$ | $CH_3$ | H | H | H | H | H |
| 17 | $SO_2$ | $CH_2Ph$ | H | H | H | H | H |
| 18 | $SO_2$ | $CH_2Ph$ | 2-Cl | 3-Cl | H | H | H |
| 19 | O | H | H | H | H | H | H |
| 20 | O | H | 2-F | 3-F | H | H | H |
| 21 | O | H | 2-Cl | 3-Cl | H | H | H |
| 22 | O | H | 2-Br | 3-Br | H | H | H |
| 23 | O | H | 2-Cl | 3-Cl | 8-$CH_3$ | H | H |
| 24 | N—CN | H | H | H | H | H | H |
| 25 | N—CN | $CH_3$ | 2-$CH_3$ | 3-$CH_3$ | H | H | H |
| 26 | N—CN | $CH_3$ | H | H | H | H | 7-$OCH_3$ |
| 27 | S | H | 2-Cl | H | H | H | H |
| 28 | S | H | 3-Cl | H | H | H | H |
| 29 | S | H | 8-Cl | H | H | H | H |
| 30 | S | H | 2-$CH_3$ | H | H | H | H |
| 31 | S | H | H | H | H | H | 7-$OCH_3$ |
| 32 | S | H | H | H | H | 8-Cl | 7-$OCH_3$ |
| 33 | S | $CH_3$ | H | H | H | 8-Cl | 7-$OCH_3$ |
| 34 | S | $CH_3$ | H | H | H | 8-Cl | 7-OH |
| 35 | S | $CH_3$ | H | H | H | H | 7-$OCH_3$ |
| 36 | S | H | H | H | H | H | 7-OH |
| 37 | S | $CH_3$ | H | H | H | H | 7-OH |
| 38 | SO | H | H | H | H | H | 7-$OCH_3$ |
| 39 | SO | $CH_3$ | H | H | H | H | 7-$OCH_3$ |
| 40 | S | $SO_2Ph$—p-Me | H | H | H | H | 7-$OCH_3$ |
| 41 | $SO_2$ | H | H | H | H | H | 7-$OCH_3$ |
| 42 | S | $COCH_3$ | H | H | H | H | 7-$OCH_3$ |
| 43 | S | $COCH_3$ | H | H | H | H | H |
| 44 | $SO_2$ | H | H | H | H | H | H |
| 45 | S | $CH_2CO_2C_2H_5$ | H | H | H | H | H |
| 46 | S | $CH_2CO_2H$ | H | H | H | H | H |
| 47 | S | $CO_2CH_3$ | H | H | H | H | H |
| 48 | S | $CH=CHCO_2CH_3$ | H | H | H | H | H |

Representative compounds of Formula I have been tested using one or more of the following assays to determine their mammalian leukotriene biosynthesis inhibiting activity and other relevant biological activities.

in buffer at a concentration of 10 cells/ml. A 500 μl aliquot of PMN suspension and test compound were preincubated for 2 minutes at 37° C., followed by the addition of 10 μM A-23187. The suspension was stirred for an additional 4 minutes then bioassayed for LTB4 content by adding an aliquot to a second 500 μl portion of the PMN at 37° C. The LTB4 produced in the first incubation caused aggregation of the second PMN, which was measured as a change in light transmission. The size of the assay aliquot was chosen to give a submaximal transmission change (usually −70%) for the untreated control. The percentage inhibition of LTB4 formation was calculated from the ratio of transmission change in the sample to the transmission change in the compound-free control.

Antigen Challenge 'in vitro' Assay

Male guinea pigs weighing 300–350 g were sensitized by injecting (I.P.) 0.5 ml of a suspension containing 0.4 mg of egg albumin (Ovalbumin, Grade V, Sigma Chemical Co.) and 4.0 g aluminum hydroxide in 19.6 ml of saline. Two weeks were permitted for sensitization to occur.

Three sensitized guinea pigs were stunned and exsanguinated. The tracheas were removed, freed of adhering tissue and divided longitudinally by cutting through the cartilaginous tissue directly opposite the muscle insertion. Each opened trachea was then transected between every second cartilage. Four of the cut sections were tied together, end to end, in a series with No. 7 silk thread ensuring that the tracheal muscles were all in the same vertical plane. Thus, each chain consisted of tissue from three different animals.

The chain so formed was then suspended under 1 g of tension (by silk ties at each end) in a 20 ml organ bath containing 10 ml of modified[1] Krebs-Henseleit buffer solution gassed with 95% $O_2$ and 5% $CO_2$ at 37° C. Mepyramine (0.55 μg/ml) and indomethacin (2.67 μg/ml) were added to the buffer to avoid the contribution of histamine receptors and cyclooxygenase products to the contraction. To record responses one end of the tracheal chain was attached to a Gould-Statham UC-2 force displacement transducer which was connected to a Beckman Type R-dynograph. The preparations were allowed to equilibrate for one hour during which time the tissues were automatically washed (10 ml volume displacement) every 6 minutes.

[1] modified Krebs solution in grams/liter and (mM): NaCl—6.87 (120); glucose—2.1 (11); NaHCO$_3$—2.1 (25); KCl—0.32 (4.72); CaCl$_2$—0.28 (2.5); MgSO$_4$. 7H$_2$O—0.11 (0.5); KH$_2$PO$_4$—0.16(1.2); pH at bathing solution=7.35±0.05.

After the equilibration period the tissues were primed with methacholine (3 μg/ml; $1.5\times10^{-5}$M), washed and allowed to recover to baseline. The tissues were treated again with a second dose of methacholine, washed, allowed to return to baseline and washed for an additional hour.

Two chains were used as a control. These were incubated in a concentration of egg albumin sufficient to induce an average contraction of 50–80% of the methacholine response.

Each compound to be tested was added to two other baths (at a final concentration in each bath of 10 μg/ml) 15 minutes prior to challenging the fresh chains with egg albumin.

The response of the challenged tissue was expressed as a percentage of the methacholine maximum. The percentage inhibition for each compound was then calculated. Compounds which at 10 μg/ml (final conc.) inhibited the egg albumin response by 50% or more were retested at a lower concentration.

Asthmatic Rat Assay

Rats were obtained from an inbred line of asthmatic rats. Both female and male rats from 200 to 300 g were used.

Egg albumin (EA), grade V, crystallized and lyophilized, was obtained from Sigma Chemical Co., St. Louis. *Bordetella pertussis* vaccine, containing $30\times10^9$ killed bacteria per ml was obtained from the Institut Armand-Frappier, Laval des Rapides, Quebec. Aluminum hydroxide was obtained from the Regis Chemical Company, Chicago.

The challenge and subsequent respiratory recordings were carried out in a clear plastic box with internal dimensions 10×6×4 inches. The top of the box was removable; in use, it was held firmly in place by four clamps and an airtight seal was maintained by a soft rubber gasket. Through the center of each end of the chamber a Devilbiss nebulizer (No. 40) was inserted via an airtight seal and each end of the box also had an outlet. A Fleisch No. 0000 pneumotachograph was inserted into one end of the box and coupled to a Grass volumetric pressure transducer (PT5-A) which was then connected to a Beckman Type R Dynograph through appropriate couplers. While aerosolizing the antigen, the outlets were open and the pneumotachograph was isolated from the chamber. The outlets were closed and the pneumotachograph and the chamber were connected during the recording or the respiratory patterns. For challenge, 2 ml of a 3% solution of antigen in saline was placed into each nebulizer and the aerosol was generated with air from a small Potter diaphragm pump operating at 10 psi and a flow of 8 liters/minute.

Rats were sensitized by injecting (s.c.) 1 ml of a suspension containing 1 mg EA and 200 mg aluminum hydroxide in saline. Simultaneously, they received an intraperitoneal (i.p.) injection of 0.5 ml of *B. pertussis* vaccine. They were used between days 14 and 18 post-sensitization. In order to eliminate the serotonin component of the response, rats were pretreated intravenously 5 minutes prior to aerosol challenge with 30 gm/kg methylserzide. Rats were then exposed to an aerosol of 3% EA in saline for exactly 1 minute, then their respiratory profiles were recorded for a further 25–30 minutes. The duration of continuous dyspnoea was measured from the respiratory recordings.

Compounds were generally administered either intraperitoneally 1 hour prior to challenge or orally 1½ hours prior to challenge. They were either dissolved in dimethylsulfoxide or suspended in 0.1% methocel and 0.5% Tween 80. The volume injected was 2 ml/kg (intraperitoneally) or 10 ml/kg (orally (p.o.)). Prior to oral treatment rats were starved overnight. Their activity was determined in terms of their ability to decrease the duration of symptoms of dyspnoea in comparison with a group of vehicle-treated controls. Usually, a compound was evaluated at a series of doses and an ED$_{50}$ was determined. This was defined as the dose (mg/kg) which would inhibit the duration of symptoms by 50%.

PAF-Induced Hyperalgesia Assay

Female Sprague-Dawley rats, 35–40 g were fasted overnight. Platelet activating factor, PAF, (L-lecithin B-acetyl O-alkyl) 1 μg/0.1 ml was given by subplantar injection in the rat paw. The compounds to be evaluated were homogenized in Aqueous Vehicle (0.9% benzyl alcohol, 0.5% Tween 80 and 0.4% methylcellulose) and administered orally in a volume of 0.1 ml, 30 minutes prior to PAF.

Animals were tested 1, 2, 3 and 4 hours after PAF administration. The vocalization threshold, defined as the pressure (mmHg) needed to evoke a squeak response, was recorded for both the injected and contralateral paw. No animal was subjected to pressure greater than 60 mmHg. Hyperalgesia is defined as a decrease in vocalization threshold as compared to a normal paw. Percent inhibition of hyperalgesia was calculated as the proportion of animals with vocalization thresholds greater than 200% of controls.

Tables II and III below show data obtained using the above described assays with representative compounds of Formula I.

TABLE II

Assay Results

| Compound | PMN $I_{50}$ μg/ml | Antigen Challenge % Inhibition and μg/ml |
|---|---|---|
| [N-NH-phenyl, pyrimidine-thiazole] | 5 | 85% (10) |
| [Me on N; phenyl with Cl, OH] | 0.2 | — |
| [Me on N (M); phenyl] | 1-5 | — |
| [H on N; phenyl with OCH₃] | 0.05-0.5 | 42% (3) |
| [Me on N; phenyl with OH] | 1-5 | 71% (3) |
| [COMe on N; phenyl] | — | 14% (3) |

TABLE II-continued

Assay Results

| Compound | PMN $I_{50}$ μg/ml | Antigen Challenge % Inhibition and μg/ml |
|---|---|---|
| [CH₂CO₂Et on N; phenyl] | — | 22% (3) |
| [Me on N; phenyl with Cl, OCH₃] | 5 | — |
| [H on N; phenyl with Cl, OCH₃] | 1 | — |
| [H on N; phenyl; O instead of S] | 0.5-1 | 35% (3) |

TABLE III

| Compound | Asthmatic Rat % Inhibition, Dose | PAF % Inhibition, Dose |
|---|---|---|
| [H on N; phenyl] | 30% 5 mg/kg, p.o. | 70% 10 mg/kg, i.p. |
| [Me on N; phenyl with Cl, OH] | 47% 5 mg/kg, p.o. | — |
| [Me on N; phenyl with OCH₃] | 43% 3 mg/kg, p.o. | — |

TABLE III-continued

| Compound | Asthmatic Rat % Inhibition, Dose | PAF % Inhibition, Dose |
|---|---|---|
| [imidazo-thiazine with phenol, Me substituent] | 39% 3 mg/kg, p.o. | — |
| [imidazo-thiazine S-oxide with methoxyphenyl, Me substituent] | 25% 3 mg/kg, p.o. | — |

The cytoprotective activity of a compound may be observed in both animal and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer Assay

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The magnitude of a prophylactic or therapeutic dose of a compound of Formula I will, of course, vary with the nature of the severity of the condition to be treated and with the particular compound of formula I and its route of administration. In general, the daily dose range for anti-asthmatic, anti-allergic or anti-inflammatory use and, generally, uses other than cytoprotection, lies within the range of from about 10 micrograms to about 20 mg per kg body weight of a mammal. This dosage may be administered in single or divided individual doses.

As cytoprotective agents, the leukotriene inhibitors of Formula I may generally be administered at a dosage range of 0.01 mg/kg to 20 mg/kg of body weight. The exact amount of inhibitor to be used will depend on, inter alia, whether it is being administered to heal damaged cells or to avoid future damage, on the nature of the damaged cells (e.g., gastro-intestinal ulcerations vs. nephrotic necrosis), and on the nature of the causative agent. An example of the use of a compound of the Formula I in avoiding future damage would be co-administration of a compound of the Formula I with a non-steroidal antiinflammatory drug (NSAID) that might otherwise cause such damage (for example, indomethacin). For such use, the compound of Formula I is administered from 30 minutes prior up to 30 minutes after administration of the NSAID. Preferably, it is administered prior to or simultaneously with the NSAID (for example, in a combination dosage form).

The effective daily dosage level for compounds of Formulae I inducing cytoprotection in mammals, especially humans, will generally range from about 0.01 mg/kg to about 20 mg/kg, preferably from about 0.01 mg/kg to about 10 mg/kg. The dosage may be administered in single or divided individual doses.

Any suitable route of administration may be employed for providing a mammal, especially a human with an effective dosage of a leukotriene inhibitor. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.01 mg to about 20 mg (preferably from about 0.1 mg to about 10 mg) of a compound of formula I per kg of body weight per day and for cytoprotective use from about 0.01 mg to about 20 mg (preferably from about 0.1 mg to about 10 mg) of a compound of Formula I per kg of body weight per day. In the case where an oral composition is employed, a suitable dosage range for anti-asthmatic, anti-inflammatory or anti-allergic use is, e.g. from about 0.1 to about 20 mg of a compound of formula I per kg of body weight per day, preferably from about 1 mg to about 10 mg per kg and for cytoprotective use from about 0.01 mg to about 20 mg (preferably from about 0.1 mg to about 10 mg) of a compound of Formula I per kg of body weight per day.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release capsules and the like. Parenteral dosage forms include solutions, emulsions and the like. Dosage forms for administration by inhalation including sprays, aerosols and the like. These inhalation formulations may be administered in metered doses ranging from about 0.1 micrograms to about 200 micrograms, administered as needed.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

For treating allergies or allergic reactions, such as allergic conjunctivitis, allergic rhinitis and the like, the Formula I compound may be administered by any conventional mode, e.g., orally, parenterally, topically, subcutaneously, by inhalation and the like. The oral and parenteral dosage forms are the same type as for the pulmonary treatment. The topical application dosage forms include ointments, salves, controlled release patches, emulsions, solutions, thixotropic formulations, powders, sprays and the like. For topical application, the percent by weight active ingredient (Formula I compound) may vary from about 0.001 to about 10%.

For treating inflammation the mode of administration may be oral, parenteral, by suppository and the like. The various dosage forms are the same as those described above.

For treating skin diseases such as psoriasis, atopic dermatitis and the like, oral, topical or parenteral administration is useful. For topical application to the diseased area salves, patches, controlled release patches, emulsions, etc., are convenient dosage forms.

For use as an analgesic, i.e., for treating pain, any suitable mode of administration may be used, e.g., oral, parenteral, by insufflation, by suppository and the like.

For treating cardiovascular conditions such as angina pectoris, etc., any suitable mode of administration, e.g. oral, parenteral, topical, insufflation, etc. and dosage form e.g. pills, liquid formulations, controlled release capsules, controlled release skin patches, etc. may be used.

In practical use, leukotriene inhibitors of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the leukotriene inhibitors of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Dosage forms for application to treat the eye are also disclosed in U.S. Pat. No. 4,348,398.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following, prepared by conventional compounding procedures, are examples of representative pharmaceutical dosage forms:

| Injectible Suspension | mg/mL |
|---|---|
| Compound of Formula I | 1–100 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Aerosol for Oral Inhibition | mg/can (200 doses/can) | |
|---|---|---|
| Compound of Formula I | 2–40 | |
| Oleic Acid | 0.2–4.0 | |
| Trichloromonofluoro methane | 5,000–8,000 | To a total |
| Dichloromonofluoro methane | 15,000–12,400 | of 20,400 |

| Cream | mg/g |
|---|---|
| Compound of Formula I | 1–100 |
| Cetyl alcohol | 130.0 |
| Sodium Lauryl Sulfate | 15.0 |
| Propylene Glycol | 100.0 |
| Methyl paraben | 1.8 |
| Propyl paraben | 1.2 |

| Cream | mg/g |
|---|---|
| Purified Water of sufficient quantity to make total 1 g | |

| Ointment | mg/g |
|---|---|
| Compound of Formula I | 1-100 |
| Methyl paraben | 1.8 |
| Propyl paraben | 1.2 |
| Petrolatum of sufficient quantity to make total 1 g | |

| Tablet | mg/tablet |
|---|---|
| Compound of Formula I | 0.2-350 |
| Microcrystalline Cellulose | 0-349.8 |
| Providone | 14.0 |
| Microcrystalline Cellulose | 90.0 |
| Pregelatinized Starch | 43.5 |
| Magnesium Stearate | 2.5 |
| | 500 |

| Capsule | mg/capsule |
|---|---|
| Compound of Formula I | 0.2-350 |
| Lactose Powder | 248.5-598.3 |
| Magnesium Stearate | 1.5 |
| | 600 |

In addition to the compounds of Formula I, the pharmaceutical compositions can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID, the weight ratio of the compound of the Formula I to the NSAID will generally range from about 1000:1 to about 1:1000, preferably 200:1 to about 1:200. Combinations of a compound of the Formula I and other active ingredients will generally also be within the aforementioned range, but in each case, an effective dose of each active ingredient should be used.

Combinations of a compound of the Formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structually related acetic acid derivatives having similar analgesic and antiinflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

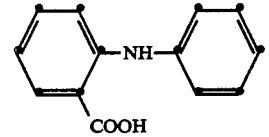

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

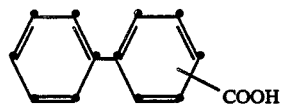

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam and 4- hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

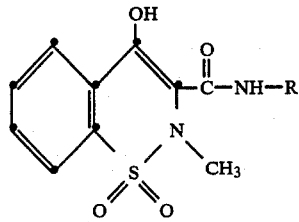

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITCl, ITF, ITF182, KB1043, KC8973, KCNTEI6090, KME4, LA2851, LT696, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent applications Ser. Nos. 539,342, filed Oct. 5, 1983, 459,924, filed Jan. 21, 1983, 539,215, filed Oct. 5, 1983, and 547,161, filed Oct. 31, 1983, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an H₁ or H2-receptor antagonist, such as for instance cimetidine, ranitidine, terfenadine, famotidine, aminothiadiazoles disclosed in EP No. 81102976.8 and like compounds, such as those disclosed in U.S. Pat. Nos. 4,283,408; 4,362,736; 4,394,508; European Patent Application No. 40,696 and a pending U.S. application Ser. No. 301,616, filed Sept. 14, 1981. The pharmaceutical compositions may also contain a $K^+/H^+$ATPase inhibitor such as omeprazole, disclosed in U.S. Pat. No. 4,255,431, and the like. Each of the references referred to in this paragraph is hereby incorporated herein by reference.

Another embodiment of the present invention are certain novel compounds encompassed by Formula I. These compounds are shown in Table IV.

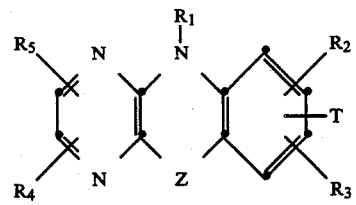

TABLE IV

NOVEL COMPOUNDS

| Z | $R_1$ | $R_2$ | $R_3$ | $R_4$ | $R_5$ | T |
|---|---|---|---|---|---|---|
| S | H | H | H | H | H | 7-OCH₃ |
| S | H | H | H | H | 8-Cl | 7-OCH₃ |
| S | CH₃ | H | H | H | 8-Cl | 7-OCH₃ |
| S | CH₃ | H | H | H | 8-Cl | 7-OH |
| S | CH₃ | H | H | H | H | 7-OCH₃ |
| S | H | H | H | H | H | 7-OH |
| S | CH₃ | H | H | H | H | 7-OH |
| SO | H | H | H | H | H | 7-OCH₃ |
| SO | CH₃ | H | H | H | H | 7-OCH₃ |
| S | SO₂Ph—p-Me | H | H | H | H | 7-OCH₃ |
| SO₂ | H | H | H | H | H | 7-OCH₃ |
| S | COCH₃ | H | H | H | H | 7-OCH₃ |
| S | COCH₃ | H | H | H | H | H |
| SO₂ | H | H | H | H | H | H |
| S | CH₂CO₂C₂H₅ | H | H | H | H | H |
| S | CH₂CO₂H | H | H | H | H | H |
| S | CO₂CH₃ | H | H | H | H | H |

TABLE IV-continued

NOVEL COMPOUNDS

| Z | R₁ | R₂ | R₃ | R₄ | R₅ | T |
|---|---|---|---|---|---|---|
| S | CH=CHCO₂CH₃ | H | H | H | H | H |

The following examples are provided to aid in the interpretation of the claims appearing below. They are not intended as a limitation upon the scope of said claims. All temperatures are in degrees Celsius.

EXAMPLE 1

Preparation of 1,4-diazaphenoxazine Step A: Sodium (1.15 g) was dissolved in iso-propanol (250 ml) with brief refluxing. The solution was cooled to room temperature and 2,3-dichloropyrazine (7.45 g) and ortho aminophenol (5.45 g) were added. The mixture was heated at reflux for 4 hours, cooled to room temperature and evaporated to about one-quarter volume in vacuo. To the black solution was added water (200 ml) with stirring. A solid precipitate was collected by filtration. The brown solid was recrystallized from MeOH/H₂O (2:1) to yield 6.3 g of fluffy brown needles. A second recrystallization afforded off-white needles, m.p. 88°–89°.

Analysis, Calculated: C, 54.19; H, 3.64; N, 18.96; Cl, 15.99. Observed: C, 54.25; H, 3.54; N, 18.60; Cl, 15.76.

Step B: A mixture of the compound from Step A (1 g) in pyridine (20 ml) was refluxed for 4 hours. DBU (2 ml) was added and the solution refluxed an additional 5 hours. The reaction mixture was diluted by the slow addition of water (100 ml). The resulting precipitate was collected by filtration, washed with water and air dried. Recrystallization from ethanol afforded the title compound, m.p. 230°–232°.

Analysis, Calculated: C, 64.86; H, 3.81; N, 22.69. Observed: C, 64.93; H, 3.80; N, 22.44.

EXAMPLE 2

1,4-Diazaphenothiazine

Step A: Preparation of ortho-(2-chloro-3-pyrazinyl)-thioaniline

To a solution of 2,3-dichloropyrazine (7.45 g, 50 mmoles) and ortho-aminothiophenol (6.25 g, 50 mmoles) in tetrahydrofuran (50 ml) was added dropwise a solution of triethylamine (6 g) in THF (25 ml) over a period of 10 minutes. A cold water bath was used to control the modest exotherm and maintain the temperature below 20°. The triethylamine chloride was removed by filtration and the filtrate was evaporated to yield a solid that was slurried for 1 hour in methanol (75 ml). The solid thus obtained was recrystallized from methanol to yield the title compound, m.p. 130°–135° (dec.).

Analysis, Calculated: C, 50.53; N, 3.39; N, 17.68; S, 13.49; Cl, 14.91. Observed: C, 50.68; N, 3.37; N, 17.56; S, 13.38; Cl, 14.54.

Step B: Preparation of 1,4-diazaphenothiazine 1,4-Diazaphenothiazine can be prepared by heating the title compound of Step A of this example with DBU in pyridine.

It was also prepared according to Cheeseman, *Tetrahedron* 33 827 (1973) to yield 1,4-diazaphenothiazine m.p. 190°–193°. Lit. 190°–192°.

EXAMPLE 3

7-Methoxy-1,4-diaza-10H-phenothiazine

5-Methoxy-2-aminothiophenol (5.5 g, 35.4 mmole) 2,3-dichloropyrazine (5.4 g, 36.2 mmoles), sodium carbonate (7.8 g, 73.6 mmoles) in 30 ml o-dichlorobenzene was refluxed until a vigorous reaction took place. Heating was stopped, the reaction mixture was cooled to room temperature, poured in water (50 ml), stirred for 30 minutes, filtered, washed with water and air-dried to yield the title compound, m.p. 210°–211° after recrystallization from ethanol-acetone.

Analysis, Calculated: C, 57.13; H, 3.92; N, 18.17; S, 13.86. Observed: C, 57.23; H, 3.82; N, 17.94; S, 14.04.

EXAMPLE 4

7-Methoxy-1,4-diaza-10-methylphenothiazine 10H-7-Methoxy-1,4-diazaphenothiazine (2.3 g, 10 mmoles) in glyme (50 ml) was heated with NaH (500 mg) when N₂ evolution subsided within 30 minutes, a red solution was obtained and treated with excess CH₃I (5 ml). Reflux was maintained for 15 minutes. The mixture was absorbed on silica gel and elution with 30% EtOAc in hexane yield successively 1.8 g of the title compound, m.p. 109°–111° and 0.23 g of the isomeric 7-methoxy-1-methyl-1,4-ciazaphenothiazine, m.p. 128°–130°.

Title compound:
Analysis, Calculated: C, 58.76; H, 4.52; N, 17.13; S, 13.07. Observed: C, 58.64; H, 4.48; N, 17.00; S, 12.92.

Isomeric compound:
Analysis, Calculated: C, 58,76; H, 4.52; N, 17.13; S, 13.07. Observed: C, 58.87; H, 4.68; N, 17.03; S, 13.15.

EXAMPLE 5

7-Hydroxy-1,4-diaza-10H-phenothiazine

Sodium hydride (60 mg, 2.5 mmoles) was added to ethanethiol (124 mg, 2 mmoles) in dry DMF (2 ml) under argon. 7-Methoxy-1,4-diaza-10H-phenothiazine (462 mg, 2 mmoles) was then added and the reaction mixture was refluxed for 3 hours. The mixture was poured into 0.5N HCl (50 ml). The solid was collected, washed with methanol and air-dried to yield starting material. Extraction of the filtrate with ethyl acetate gave 100 mg of a mixture that was chromatographed on silica gel, eluting with 40% ethyl acetate in hexane to yield 25 mg of the title compound.

Analysis, Calculated: C, 55.19; H, 3.25; N, 19.34; S, 14.76. Observed: C, 55.19; H, 3.37; N, 19.12; S, 14.86.

EXAMPLE 6

7-Hydroxy-1,4-diaza-10-methylphenothiazine

Following a procedure identical to that described in Example 5, 7-methoxy-1,4-diaza-10-methylphenothiazine was converted to the title compound, m.p. 207–208.5°.

Analysis, Calculated: C, 57.13; H, 3.92; N, 18.17; S, 13.86. Observed: C, 57.16; H, 3.97; N, 18.26; S, 13.81.

EXAMPLE 7

7-Methoxy-1,4-diaza-10H-10-acetyl phenothiazine

A mixture of 7-methoxy-1,4-diaza-10H-phenothiazine (4.62 g, 20 mmoles) and sodium acetate (2.5 g) in acetic anhydride (50 ml) was refluxed for 18 hours. The reaction mixture was cooled to room temperature. The resulting crystals were filtered, washed with dilute acetic acid and air dried to yield 5.0 g of the title compound, m.p. 221°–223°.

EXAMPLE 8

7-Methoxy-1,4-diaza-10-methylphenothiazine

To a suspension of sodium hydride (0.5 g, 20.8 mmoles) in dimethoxy ethane (50 ml) was added 7-methoxy-1,4-diaza-10H-phenothiazine (2.3 g, 10 mmoles). After stirring for 30 minutes, a deep red colored solution of the anion was obtained and was quenched by adding excess methyl iodide (5 ml). The reaction mixture was poured on ice and the resulting mixture was extracted with ethyl acetate, washed with brine, dried ($Na_2SO_4$) and evaporated to dryness. The residue was chromatographed on silica gel, yielding 1.8 g of the title compound, m.p. 109°–111°.

Also obtained was 0.28 g of isomeric 3-methoxy-6,9-diaza-9-methylphenothiazine, m.p. 128°–130°.

EXAMPLE 9

1,4-Diaza-10-methylphenothiazine

Similarly, using the procedure of Example 8, substituting 1,4-diaza-10H-phenothiazine for 3-methoxy-1,4-diaza-10H-phenothiazine, the title compound, m.p. 101°–102°, was obtained.

The isomeric 1,4-diaza-1-methylphenothiazine, m.p. 101°–102° was also obtained.

EXAMPLE 10

1,4-Diazaphenothiazine-5-oxide

To 1,4-diaza-10H-phenothiazine (1 g, 5 mmoles) in acetic acid (15 ml) was added 50% hydrogen peroxide (1 ml). The mixture was stirred at 55° for 30 minutes. The mixture was evaporated to a small volume and the title compound crystallized out. The crystals were filtered, washed with acetic acid and air dried to yield 983 mg of the title compound, m.p. 261°–263°.

EXAMPLE 11

7-Methoxy-1,4-diazaphenothiazine-5-oxide

Similarly, as in Example 10, but substituting 7-methoxy-1,4-diazaphenothiazine for 1,4-diazaphenothiazine, the title compound, m.p. 240°–241°, was obtained in an 87% yield.

EXAMPLE 12

1,4-Diazaphenothiazine-5,5-dioxide

Similarly, by carrying out the reaction described in Example 10, but at 80° instead of 55°, the title compound, m.p. 316°–318°, was obtained.

EXAMPLE 13

7-Methoxy-1,4-diazaphenothiazine-5,5-dioxide

Similarly, as in Example 10, but substituting 7-methoxy-1,4-diazaphenothiazine for 1,4-diazaphenothiazine and carrying out the reaction at 80° instead of 55°, the title compound, m.p. 293°–294°, was obtained.

EXAMPLE 14

7-Methoxy-10-methyl-1,4-diazaphenothiazine-5-oxide

Similarly, as in Example 10, but substituting 7-methoxy-10-methyl-1,4-diazaphenothiazine for 1,4-diazaphenothiazine, the title compound, m.p. 229°–231° was obtained in 67% yield.

EXAMPLE 15

1,4-Diaza-10-carboethoxymethylphenothiazine

Following the conditions of Example 4 but substituting ethyl bromoacetate for methyl iodide, the title compound, m.p. 115°–117°, was obtained.

The isomeric 1,4-diaza-1-carboethoxymethyl phenothiazine m.p. 157°–158°, was also obtained.

EXAMPLE 16

1,4-Diaza-10-carboxymethylphenothiazine 1,4-Diaza-10-carboethoxymethylphenothiazine (862 mg, 3 mmoles) in methanol (17 ml) was treated with 5N sodium hydroxide (1 ml). The mixture was refluxed for 2 hours. Water (17 ml) was added and the solution was acidified with 6N hydrochloric acid (1 ml). The title compound, m.p. 197°–198°, was isolated by filtration in a yield of 84%.

EXAMPLE 17

10-Acetyl-1,4-diazaphenothiazine

By following the conditions of Example 7, but substituting 1,4-diazaphenothiazine for 3-methoxy-1,4-diazaphenothiazine, the title compound, m.p. 174°–175°, was obtained in an 89% yield.

EXAMPLE 18

10-Carbomethoxy-1,4-diazaphenothiazine

By following the conditions of Example 4, but substituting 1,4-diazaphenothiazine for 7-methoxy 1,4-diazaphenothiazine and methylchloroformate for methyl iodide, the title compound, m.p. 137°–138° was obtained in a 23% yield.

EXAMPLE 19

8-Chloro-1,4-diaza-7-methoxyphenothiazine

Following the conditions of Cheeseman et al., (*Tetrahedron* 33, 827 (1977)), the reaction of 2,3-dichloropyrazine with 2-amino-4-chloro-5-methoxythiophenol gave the title compound, in a 25% yield.

Analysis, Calculated: C, 4972; H, 3.03; N, 15.81; S, 13.34. Observed: C, 49.70; H, 2.83; N, 15.84; S, 13.54.

EXAMPLE 20

8-Chloro-7-methoxy-1,4-diaza-10-methylphenothiazine

By following the conditions of Example 4, but substituting 8-chloro-7-methoxy-1,4-diaza-phenothiazine for 7-methoxy-1,4-diazaphenothiazine, the title compound was obtained in a 50% yield.

Analysis, Calculated: C, 51.52; H, 3.60; N, 15.02; Cl, 12.67; S, 11.46. Observed: C, 51.66; H, 3.79; N, 14.84; Cl, 12.61; S, 11.71.

EXAMPLE 21

8-Chloro-7-hydroxy-1,4-diaza-10-methylphenothiazine

By following the conditions of Example 5, but substituting 8-chloro-7-methoxy-1,4-diaza-10-methyl-phenothiazine for 7-methoxy-1,4-diazaphenothiazine, the title compound was obtained in a 90% yield.

Analysis, Calculated: C, 49.72; H, 3.03; N, 15.81; S, 12.07, Cl, 13.34. Observed: C, 49.60; H, 3.19; N, 15.75; S, 12.11; Cl, 13.21.

EXAMPLE 22

10-(2-Carbomethoxyvinyl)-1,4-diazaphenothiazine

To a suspension of sodium hydride (0.1 g, 4.2 mmoles) in dimethoxyethane (10 ml) was added 1,4-diazaphenothiazine (200 mg, 1 mmole). After stirring for 30 minutes a deep red solution of the anion was obtained and this was treated with methylpropiolate (85 μl, 1.0 mmole). Stirring was maintained for 30 minutes. The mixture was evaporated to dryness and the residue was purified by chromatography. Elution with 40% EtOAc/hexane gave the desired product as on orange solid, m.p. 165°–169°. NMR analysis showed the product to be a mixture of trans and cis isomers in a ratio of 4 to 1.

EXAMPLE 23

7-Methoxy-10-p-toluenesulfonyl-1,4-diazaphenothiazine

To a cooled, stirred suspension of 1,4-diazaphenothiazine (2.31 g, 10 mmole) in glyme (23 ml) was added portionwise sodium hydride (300 mg). After stirring the mixture at room temperature for one hour, the mixture was again cooled in an ice-bath and p-tosylchloride (1.9 g, 10 mmole) was added in portions. An additional 200 mg of sodium hydride was added and the solution stirred at room temperature for one hour. Water was cautiously added, and the phases were separated. The organic phase was washed with water and dried. The title compound slowly crystallized from the organic solvent. The crude title compound was recrystallized from ethyl acetate/diisopropyl ether (2:1).

Analysis Calculated: C, 56.09; H, 3.92; H, 10.90; S, 16.64. Observed: C, 56.03; H, 4.00; N, 10.83 S, 16.81.

EXAMPLE 24

9-Oxo-10-trifluoroacetyl-9,10-dihydro-pyrazino[2,3-b]pyrrolo[1,2,3-d,e][1,4]benzothiazine A suspension of the acid from Example 16 (2.59 g, 10 mmole) in methylene chloride (78 ml) was treated with trifluoroacetic anhydride (1.55 ml, 2.31 g, 11.0 mmole). The mixture was stirred at room temperature overnight, and then evaporated. The residue was dissolved in ethylene chloride and the solution evaporated onto silica gel (13 g). The solid was placed on a column of silica gel (100 g) and elution with 1:1 ethyl acetate/hexane gave 878 mg of title compound.

Analysis, Calculated: C, 49.86; H, 1.79; N, 12.46; S, 9.50; F, 16.90. Observed: C, 49.69; H, 2.02; N, 12.22; S, 10.07; F: 16.67.

In those instances where asymmetric centers are present, more than one stereoisomer is possible, and all possible isomeric forms are deeded to be included within the planar structural representation shown. Optically active (R) and (S) isomers may be resolved using conventional techniques known to the skilled artisan.

What is claimed is:

1. A compound of Formula I:

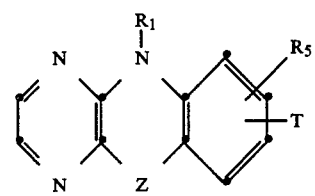

wherein the substituents are selected from:

| Z | $R_1$ | $R_5$ | T |
|---|---|---|---|
| S | H | H | 7-OCH$_3$ |
| S | H | 8-Cl | 7-OCH$_3$ |
| S | CH$_3$ | 8-Cl | 7-OCH$_3$ |
| S | CH$_3$ | 8-Cl | 7-OH |
| S | CH$_3$ | H | 7-OCH$_3$ |
| S | H | H | 7-OH |
| S | CH$_3$ | H | 7-OH |
| SO | H | H | 7-OCH$_3$ |
| SO | CH$_3$ | H | 7-OCH$_3$ |
| S | SO$_2$Ph—p-Me | H | 7-OCH$_3$ |
| SO$_2$ | H | H | 7-OCH$_3$ |
| S | COCH$_3$ | H | 7-OCH$_3$ |
| S | COCH$_3$ | H | H |
| S | CH$_2$CO$_2$C$_2$H$_5$ | H | H |
| S | CH$_2$CO$_2$H | H | H |
| S | CO$_2$CH$_3$ | H | H |
| S | CH=CHCO$_2$CH$_3$ | H | H. |

2. 7-Methoxy-1,4-diaza-10-methylphenothiazine, according to claim 1.

3. 7-Hydroxy-1,4-diaza-10H-phenothiazine, according to claim 1.

4. 7-Hydroxy-1,4-diaza-10-methylphenothiazine, according to claim 1.

5. 7-Methoxy-1,4-diaza-10-methylphenothiazine, according to claim: 1.

6. 8-Chloro-1,4-diaza-7-methoxyphenothiazine, according to claim 1.

7. 8-Chloro-7-methoxyl-1,4-diaza-10-methylphenothiazine, according to claim 1.

8. 8-Chloro-7-hydroxy-1,4-diaza-10-methylphenothiazine, according to claim 1.

* * * * *